United States Patent [19]

Gestrelius

[11] 4,288,552
[45] Sep. 8, 1981

[54] IMMOBILIZED INTRACELLULAR ENZYMES

[75] Inventor: Stina M. Gestrelius, Farum, Denmark

[73] Assignee: Novo Industri A/S, Denmark

[21] Appl. No.: 29,156

[22] Filed: Apr. 11, 1979

[30] Foreign Application Priority Data

Apr. 19, 1978 [GB] United Kingdom ............... 15521/78

[51] Int. Cl.³ ...................... C12N 11/00; C12N 11/16; C12N 11/02
[52] U.S. Cl. ..................................... 435/174; 435/175; 435/177; 435/180; 435/822; 435/832; 435/911
[58] Field of Search .................. 435/94, 174, 175, 177, 435/181, 182, 180, 253, 254, 832, 822, 911

[56] References Cited

U.S. PATENT DOCUMENTS

| | | | |
|---|---|---|---|
| 3,779,869 | 12/1973 | Zienty | 435/174 |
| 3,796,634 | 3/1974 | Haynes et al. | 435/180 |
| 3,957,580 | 5/1976 | Nelson | 435/174 X |
| 3,980,521 | 9/1976 | Amotz et al. | 435/174 |
| 3,989,596 | 11/1976 | Long | 435/174 |

*Primary Examiner*—David M. Naff
*Attorney, Agent, or Firm*—Fidelman, Wolffe & Waldron

[57] ABSTRACT

Intracellular glutaraldehyde sensitive enzymes are immobilized by reacting microbial cell material with glutaraldehyde in the presence of a polyamine which is preferably a branched polyethylene imine.

15 Claims, No Drawings

IMMOBILIZED INTRACELLULAR ENZYMES

THIS INVENTION relates to the immobilization of intracellular enzymes, and in particular is directed to immobilization of intracellular enzymes sensitive to glutaraldehyde.

INTRODUCTION

In recent years conduct of enzyme catalyzed reactions with an immobilized enzyme has become attractive to industry. The large scale isomerization of glucose syrups into a glucose-fructose mixture isosyrup with immobilized glucose-isomerase for example.

Different methods for preparation of immobilized enzymes are described in Methods in Enzymology, Vol. 44 (1977) Academic Press. Most of these methods involve particulate supports with the inherent disadvantages of the high price of the support and the unavoidable high dilution of the enzymatic activity.

Of the many immobilization procedures, and immobilized enzyme forms now known to the art, the system believed to be the best (to date) for immobilization of intracellular enzymes involves reaction with glutaraldehyde.

The intracellular enzyme, normally produced initially as nothing more than a collected mass of microorganism cells is converted into a cell mass particulate form through reaction of the substance of the cells and glutaraldehyde, with or without co-reactants such as proteins. For the details of diverse methods for converting (glucose isomerase) microorganism cells into cell mass particulate form by reaction with glutaraldehyde reference is made to U.S. Pat. No. 3,980,521. The whole microbial cells may themselves be treated with glutaraldehyde under conditions which stabilize the enzyme activity using for example, the procedure of U.S. Pat. No. 3,974,036.

Glutaraldehyde is a preferred cross-linking reagent. It is accepted by health authorities, and may be the best known, most widely used enzyme immobilizing or cross-linking agent.

While many intracellular enzymes can be glutaraldehyde cross-linked without unacceptable loss in enzyme activity, e.g., glucose isomerase, some enzymes can not. In particular, thiol-enzymes, namely enzymes with an SH group in or very near the active site of the enzyme molecule are inactivated by thiol-reactive agents, for example, glutaraldehyde. Instances of such enzymes are urease and dehydrogenases. Thus, there exists a class of glutaraldehyde sensitive enzymes, i.e., an enzyme that loses more than 75% of its original activity when it is immobilized by glutaraldehyde treatment of the cells containing the enzyme according to the immobilization methods described in U.S. Pat. No. 3,980,521 and German Offenlegungsschrift no. 2,223,340 to form a particulate product of an acceptable physical strength for industrial applications.

Thus, efforts to immobilize glutaraldehyde sensitive intracellular enzymes according to the procedures of U.S. Pat. No. 3,980,521 invariably results in severe loss of enzyme activity.

RATIONALE OF THE INVENTION

The objective of this invention is to apply the processing and production advantages of the glutaraldehyde immobilization system to glutaraldehyde sensitive intracellular enzymes.

One object of the present invention is to provide a process for immobilization of intracellular, glutaraldehyde sensitive enzymes, using gluataraldehyde as a cross-linking agent under circumstances where the immobilized enzyme may be manufactured in a high yield, at a relatively low price and with a relatively small dilution of enzymatic activity. Achievement of this objective enables the production of a product comprising immobilized enzyme which is well suited for industrial applications.

A further object of the present invention is to provide glutaraldehyde immobilized intracellular glutaraldehyde sensitive enzymes in the form of a microbial cell preparation. Within the context of this invention the term microbial cell material is intended to include both whole microorganism cells, as well as fragmented cells or homogenized cells. The term microbial cell preparation is intended to include whole microorganism cells as well as cell mass particulate forms of immobilized intracellular enzymes.

THE INVENTION

Briefly stated the process of this invention comprises reacting intracellular enzyme with glutaraldehyde in the presence of a water soluble polyamine in an aqueous medium. The molecular weight of the polyamine should exceed about 500, 500–100,000 Daltons being a suitable range, and the polyamine molecule should contain a number of primary amine groups thereon. The content of primary amino groups should exceed 5%, and preferably 20% of the total amino groups, i.e., primary, secondary and tertiary amino groups. Branched polyethylene imine is a preferred polyamine. A branched polyethylene imine will have a primary: secondary: tertiary amino group ratio of 1:2:1. The ratio of polyamine to glutaraldehyde on a wt/wt basis is 1:5 to 5:1, if the polyamine is a branchet polyethylene imine.

DISCUSSION OF THE INVENTION

Surprisingly, the presence of the polyamine results in a very high recovery of the enzyme activity. Without polyamine in the reaction mixture, the yield of enzyme activity may be so low as 0 to 15%, whereas the yield with polyamine present may be of the order of magnitude of from 30 to 80% No inert particulate support is needed and the dilution of the enzymatic activity is, therefore, small.

When performing the immobilization, the polyamine is added to the microbial cells before or simultaneously with the glutaraldehyde. If the glutaraldehyde is added to the microbial cells first, the recovery of enzymatic activity in the immobilized product will be reduced significantly, unless the polyamine is added very soon after the glutaraldehyde addition, depending on temperature, concentration and similar parameters. It is believed that the primary amino groups in the polyamine react with the glutaraldehyde to form stable cross-links. Tests conducted with polyethylene imines modified through reaction of the primary (and secondary) amino groups therein with an epoxy compound indicate that the so modified polyethylene imines fail to prevent deactivation of the enzyme.

It is to be understood that the relative amounts and condition of microbial cells to the glutaraldehyde and polyamine should be chosen in such a way that the immobilized enzyme product is suited for the intended industrial purposes; that is, the product should have a high enzymatic activity, a high activity yield (in comparison with the total enzyme activity before immobilization), a high enzyme stability all along with the enzyme form desired, e.g., particles of high mechanical stability.

A preferred embodiment of the invention comprises the immobilization of the glutaraldehyde sensitive penicillin V-acylase produced by the species of the bacterial strain NRRL 11240 (other strains essentially identical to NRRL 11240 including mutants and variants thereof can be expected to produce the enzyme). Additional preferred embodiments of the invention comprises the immobilization of urease manufactured by means of a strain belonging to the species *Bacillus pasteurii,* of lactase manufactured by means of a strain belonging to the species *Kluyveromyces fragilis* and also of a malolactic enzyme manufactured by means of a strain belonging to the species *Leuconostoc oenos.*

A preferred embodiment of the invention comprises reacting whole microbial cells.

One embodiment of the invention adopted particularly to treatment of whole cells comprises the use of the aqueous part of the fermentation broth as the aqueous medium. This embodiment comprising the direct treatment of the fermentation broth with glutaraldehyde and polyamine, therefore, constitutes an extremely simple and economic immobilization method.

However, the cells may be separated from the fermentation broth, for example by centrifugation, and then resuspended in water or an appropriate buffer with pH between 5 and 10, the aqueous part of this suspension being the aqueous medium which subsequently is treated with glutaraldehyde and polyamine. Likewise, the aqueous part of the cell sludge, said cell sludge being separated from the fermentation broth, for example by centrifugation and having a consistency as a tooth paste, may be used as the aqueous medium which subsequently is treated with glutaraldehyde and polyamine. Except for including polyamine in the reaction mixture, the details of the procedures described by patent 3,980,521 may be employed. In some preferred embodiments of the invention the isolated immobilized enzyme containing cell materials are shaped, preferably by granulation or extrusion. In other preferred embodiments, washed and isolated immobilized enzyme containing cell materials are shaped by drying, milling and sieving to a particle size in the range of from 100 to 1000μ, preferably from 200 to 700μ.

It is preferred to use a branched polyalkylene imine of 2-4 alkyl chain length, more preferably polyethylene imine as the polyamine.

In a further preferred embodiment of the invention a branched polyethylene imine with molecular weight between 500 and 100,000 Daltons is used as the polyamine.

It is preferred that a ratio of primary amine equivalents to aldehyde equivalents in the range of from 0.01:1 to 10:1, preferably from 0.1:1 to 1:1, is used.

A preferred embodiment of the invention comprises the sequence of adding the polyamine to the aqueous medium with the microbial cells and then adding the glutaraldehyde.

Preferably, in the process of the present invention, a ratio glutaraldehyde/microbial cells (w/w) of from 0.01 to 100, preferably from 0.1 to 10, can be used.

According to a second aspect of the present invention there is provided hereby novel immobilized enzyme products.

A further aspect of the present invention comprises the use of the immobilized enzyme product batchwise or continuously, in the latter case preferably in a column.

A preferred embodiment of the use of the immobilized enzyme product comprises use of immobilized penicillin V-acylase produced by the strain NRRL 11240 (or strains essentially identical thereto, including mutants and variants thereof), under continuous conditions.

To demonstrate the surprising activity conserving effect attributable to employment of the polyamine in combination with glutaraldehyde on the glutaraldehyde sensitive enzymes reference is made to the following comparative experiments.

a. 2 g of spray dried urease containing cells from *Bacillus pasteurii* ATCC 11859 (6200 IU/g at pH 7) were suspended in 98 ml of water with 10 μM β-mercaptoethanol. The pH of the cell suspension was 7.7 when 1.6 ml of 25% glutaraldehyde was added with stirring. After 20 min. of stirring at room temperature, the pH value declined to 6.9. The immobilized cells were filtered and washed twice with 0.5 liters of 1 mM B-mercaptoethanol solution in water. After vacuum-drying (90 min. at about 50° C.) 0.7 g of immobilized preparation was obtained with an activity of 64 IU/g, measured at optimum conditions, for a particle size of 125-300μ. This equals an activity yield of 0.3%, conditions, for a particle size of 125-300μ. This equals an activity yield of 0.3%, b. A cell-suspension identical to the one described in (a) supra was treated with 4 ml of 10% polyethylene imine (molecular weight 60 000, Dow Chemicals PEI 600), adjusted to pH 7, whereafter 2.75 ml of 25% glutaraldehyde was added. Stirring was continued for 60 min. at room temperature. After filtration, washing and drying as in (a) supra the resulting 0.75 g of immobilized cells had an activity of 5600 IU/g (125-300μ), that is the activity yield was 34%.

The definitions of the units of initial enzymatic activities of the enzymes in the following Examples appear from the following Table I.

TABLE I

| Enzyme | Determination of Initial Enzyme Activities |
|---|---|
| urease | pH-stat titration with 1 N HCl at pH 7.0 and 30° C. 3% (0.5 M) urea in 0.2 M phosphate buffer was used as a substrate 1 unit is 1 μ mol of urea hydrolyzed/minute. |
| penicillin V | Incubation at 40° C. with 3% penicillin V in 0.2 M phosphate buffer pH 7.5 After the removal of the cells the 6-APA produced was determined with p-aminobenzaldehyde according to Balasingham et al. (1972), Biochem. Biophys. Acta 276, 250-56 1 unit = 1 μ mol of 6-APA produced/minute. |
| lactase | Non-immobilized cells are first opened by treatment at room temperature with about 8% 1-butanol in 0,1 M phosphate buffer with pH 7 in 20 minutes. Incubation (at 37° C. for the Kluyveromyces fragilis lactase and at 60° C. for the NRRL B-11, 229 lactase) with 4.75% (w/v) lactase in milk buffer pH 6.5 (Das grosse Melkerei Lexikon, Schultz 1965, Vol. 2,M-Z p. 740). After removal of the cells the glucose produced was determined with Boehringer Manheim's Blood Sugar reagent (GOD-Perid method). 1 unit = 1 μ mol of glucose produced/minute. |
| malo-lactic enzyme | Incubation at 30° C. with 33 mM L-malate 1.67 mM NAD$^+$ and 0.7 mM MnCl$_2$ in 0.1 M phosphate buffer pH 5.1 After removal of the cells the lactate produced was |

TABLE I-continued

| Enzyme | Determination of Initial Enzyme Activities |
|---|---|
| | determined with LDH + NAD+ according to Gutmann, I. and Wahlefeld, A.W. (1974) in Methods of Enzymatic Analysis, 2nd ed. Vol 3, (H.U. Bergmeyer, ed.), Academic Press, p. 1463-67. 1 unit = 1 μ mol of lactate produced/minute. |

The following Examples further illustrate the present invention. The main subject matter of the examples appear from the following table.

| Enzyme | Production of immobilized enzyme | Use of immobilized enzyme | Example |
|---|---|---|---|
| Penicillin V-acylase | x | | 1-7 |
| | | x | 8-10 |
| lactase | x | | 11-13 |
| | | x | 13 |
| urease | x | | 14-15 |
| | | x | 16 |
| malolactic enzyme | x | | 12-18 |
| | | x | 19-20 |

Example 12 includes a comparison experiment without polyethylene imine.

In all the following examples the pH value of the polyethylene imine was adjusted to about 7 before addition. However, satisfactory immobilized enzymes can also be obtained by means of polyethylene imines with other pH values, e.g. in the interval from about 4 to about 9.

EXAMPLE 1

To 1 l of fermentation broth of strain NRRL 11240, containing about 1% dry cells and 1.5 penicillin V acylase units/ml, was added with stirring 30 ml of 10% polyethylene imine (branched, molecular weight 60000, PEI 600 from Dow Chemicals), followed by 25 ml of 25% glutaraldehyde after five minutes. Stirring was continued for another 60 minutes at room temperature and the immobilized cells were then filtered off, washed with phosphate buffer (50 mM pH 7) and air dried. 14.2 dried immobilized cells were obtained with an activity of 71 units/g for a particle size between 180 and 420μ, that is the activity yield was 65%.

EXAMPLE 2

To 1.5 liters of fermentation broth of strain NRRL 11240 (0.68 penicillin V acylase units/ml) was added with stirring 45 ml of 10% polyethylene imine (branched, molecular weight 600, PEI 6 from Dow Chemicals) and 30 ml of 25% glutaraldehyde at 4° C. Stirring was continued at reduced speed for another 60 min. and the multi-cell particles formed were then filtered, washed with phosphate buffer pH 7 and air-dried. The dried preparation (21 g) had a pen V acylase activity of 14.5 units/g, for a particle size of 200-700μ, that is the activity yield was 30%.

EXAMPLE 3

380 l fermentation broth of strain NRRL 11240 (2.5 penicillin V acylase units/ml) was cooled to about 15° C. and 40 l 10% polyethylene imine (Polymin P, BASF) was added with stirring, followed by 9.4 l of 25% glutaraldehyde (Union Carbide). Stirring was then continued at reduced speed for another 45 minutes, whereafter beta-mercaptoethanol was added to a final concentration of 25 mM and the immobilized cells were separated on a filter press. The wet filter cake was granulated and the granules dried in a fluid bed at 50°-55° C. 7.1 kg of dry preparation with 55 units/g (unfractionated particles) were obtained, which equals an activity yield of 41%.

EXAMPLE 4

A series of immobilized preparations from the same fermentation broth of strain NRRL 11240 as in Example 3 shows the influence of variations of the concentration of polyethylene imine at a constant addition of glutaraldehyde. The results are shown in Table II.

TABLE II

| Polyethylene imine (Polymin P) % w/v | Penicillin V acylase activity units/g dry product (200-400 μ) |
|---|---|
| 0.2 | 7 |
| 0.5 | 36 |
| 0.8 | 58 |
| 1.0 | 71 |
| 1.2 | 70 |

In each case the indicated amount of Polymin P (BASF) was added with stirring as a 10% solution to 0.5 l fermentation broth of strain NRRL 11240 (2.5 Penicillin V acylase units/g) followed by 10 ml of 25% glutaraldehyde. Stirring was continued at reduced speed for another 60 minutes, whereafter the cells were filtered off, washed with 25 mM beta-mercaptoethanol in 50 mM phosphate buffer pH 7.5 and air-dried. About 9 g dry material was obtained from each preparation.

EXAMPLE 5

To 2 liter of fermentation broth of strain NRRL 11240 (2.0 penicillin V acylase units/ml) was added 200 ml 10% polyethylene imine (Polymin P, BASF), and the cells were then concentrated to about one tenth of the original volume. 6 ml of 25% glutaraldehyde was added to the cell sludge with stirring, which was allowed to continue at reduced speed for another 60 minutes. The immobilized cells were then filtered and washed with 25 mM beta-mercaptoethanol in 50 mM phosphate buffer pH 7.5 on a glass filter. After air-drying at room temperature, 20 g of preparation with 65 units/g (200-400μ) was obtained. This equals an activity yield of about 33%.

A series of immobilized preparations made in a similar way as above described, but with varying amounts of glutaraldehyde shows the influence of variations of the glutaraldehyde concentration after a constant addition of polyethylene imine and subsequent concentration. The results are shown in the following Table III.

TABLE III

| Glutaraldehyde % w/v | Penicillin V acylase activity units/g dry preparation (200-400 μ) |
|---|---|
| 0.5 | 106 |
| 0.75 | 65 |
| 1.0 | 56 |
| 1.5 | 37 |
| 5.0 | 3 |

Between 9 and 11 g dry material was obtained from each preparation per liter of fermentation broth.

EXAMPLE 6

350 l of fermentation broth of strain NRRL 11240 (2.4 penicillin V acylase units/ml) was cooled to about 15°

C., and 24.5 l of 10% polyethylene imine (branched, molecular weight about 700, PEI 15T from Taihei Sangyo Kaisha) was added with stirring, followed by 3.5 l 50% glutaraldehyde (Union Carbide). Stirring was then continued at reduced speed for another 45 minutes, whereafter beta-mercaptoethanol was added to a final concentration of 25 mM, and the immobilized cells were separated on a membrane press. The filter cake was extruded (500μ orifice) and the particles dried in a fluid bed at 50°–55° C. The yield was 6.2 kg of dry preparation with 85 penicillin V acylase units/g (particle size below 500μ) corresponding an activity yield of 63 percent.

EXAMPLE 7

A series of immobilized preparations from the same fermentation broth of strain NRRL 11240 as in examples 3 and 4 shows the influence of using different types of polyethylene imines.

| Polyethylene imine (PEI) | Molecular wweight $\times 10^{-3}$ | % PEI (w/v) | Penicillin V-acylase activity, units/g | Yield of dry prep., g |
| --- | --- | --- | --- | --- |
| PEI 600, Dow Chemicals | 60 | 0.3 | 103 | 8 |
| Polymin HS, BASF | — | 0.8 | 50 | 16 |
| Polymin P, BASF | — | 1.0 | 70 | 10 |
| Sedipur.CL 930, BASF | (100) | 1.0 | 50 | 11 |
| PEI 15 T, Taihei Sangyo Kaisha Ltd. | 0,7 | 0,7 | 134 | 7 |
| PEI 210 T, Taihei Sangyo Kaisha Ltd. | 40–60 | 0.9 | 80 | 10 |
| Epomin P-1000, Shokubai Kagaku Kogyo Co. | 60–80 | 0.9 | 65 | 14 |
| Epomin P-500, Shokubai Kagaku Kogyo Co. | 30–40 | 0.9 | 120 | 7 |

In each case the indicated amount of polyethylene imine was added with stirring as a 10% solution of 0.5 l fermentation broth of strain NRRL 11240 (2.5 penicillin V acylase units/ml) followed by 10 ml 25% glutaraldehyde. Stirring was continued at reduced speed for another 45 min. whereafter the cells were filtered off, washed with 25 mM beta-mercaptoethanol in 50 mM phosphate buffer pH 7.5 and air dried.

EXAMPLE 8

10 g of the cells immobilized as described in Example 1 were added to 200 ml of 3% (w/v) crude K-penicillin V in 50 mM phosphate buffer pH 7.5. Deacylation was carried out at 40° C. with a stirring rate of 150 rpm and a constant pH of 7.5 (by titration with 4 N NaOH). 95% of the penicillin was converted to 6-APA in two and a half hours. The procedure could be repeated with fresh penicillin V at least 20 times without any substantial decrease in conversion. The degree of conversion was determined by HPLC (high pressure liquid chromatography), separation of the reaction mixture on Waters' μBondapak C-18 column (eluted by a gradient from 20% methyl alcohol in water to 50% methyl alcohol in water, ion pairing with Water's Pic A reagent) and subsequent uv-detection. Reference is made to Waters Associates' information booklet Paired-Ion Chromatography, D 61 May 1976, Printed in USA (Maple Street, Milford, Mass.). The results of conversion of 3% (w/v) K-penicillin V to 6-APA at 40° C. are shown in Table IV.

TABLE IV

| Batch number | Degree of conversion (%) |
| --- | --- |
| 1 | 96 |
| 2 | 97 |
| 3 | 98 |
| 4 | 98 |
| 5 | 98 |
| 6 | 98 |
| 7 | 97 |
| 8 | 97 |
| 9 | 97 |
| 10 | 97 |
| 11 | 96 |
| 12 | 97 |
| 13 | 97 |
| 14 | 97 |
| 15 | 96 |

EXAMPLE 9

9.7 g of the immobilized cells from Example 2 were added to 100 ml of 3% (w/v) K-penicillin V in 50 mM phosphate buffer pH 7.5. Deacylation was carried out at 40° C. with a stirring rate of 150 rpm and a constant pH of 7.5 by means of pH-stat. More than 90% of the penicillin was converted to 6-APA in 3 hrs. After ten consecutive batches the time of conversion had increased to about 3.5 hrs. and after 20 batches to 4 hrs.

EXAMPLE 10

Immobilized cells corresponding to a dry weight of 100 g and originating from the product of example 6 were re-swelled in 50 mM phosphate buffer of pH 7.5 containing 5 mM beta-mercaptoethanol and packed in a column with a diameter of 10 cm (bed volume 400 ml). 65 g crude K-penicillin V in 1.5 l of the same mercaptoethanol containing buffer as above was recirculated through a pre-heater to the column (held at 35° C.) and back to a reservoir (held at 12° C.) where pH was continuously adjusted to 7.5 by titration with 4 M NaOH. With a circulation rate of 14 bed volumes per hour 98% conversion of penicillin V to 6-APA was obtained after 4 hrs. After ten consecutive runs the reaction time had to be increased to 6 hrs.

EXAMPLE 11

To 500 ml fermentation broth of Kluyveromyces fragilis NRRL Y 1109 (pH adjusted to 7.5) was added with stirring 40 ml of 10% polyethylene imine (branched, molecular weight 700, PEI 15 T from Taihei Sangyo Kaisha), followed by 16 ml of 25% glutaraldehyde. After 60 min. stirring at room temperature, the particles were filtered, granulated and air-dried. The 6.5 g of dry material obtained had a lactase activity of about 500 units/g, which corresponds to about 30% of the original activity.

EXAMPLE 12

To 500 ml of fermentation broth of NRRL B-11, 229 with 5.1 lactase units/ml was added 25 ml 10% polyethylene imine (PEI 15 T from Taihei Sangyo Kaisha Co.) with stirring, followed by 10 ml 25% glutaraldehyde. Stirring was continued for one hour at room temperature, whereafter the immobilized cells were filtered off and air-dried. 4.0 g dried preparation contained 209 lactase units/g, corresponding to a yield of 33%.

In order to demonstrate the effect of the polyethylene imine a comparative experiment without polyethylene was run in the following way.

To 500 ml of fermentation broth of NRRL B-11, 229 with 5.1 lactase units/ml was added 10 ml 25% glutaraldehyde with stirring. Stirring was continued for one hour at room temperature. The treated cells were flocculated with 0.5% Superfloc (12.5 ml 20% Superfloc C 521, a cationic flocculation agent), filtered and air-dried. 3.7 g dried preparation contained 105 lactase units/g, corresponding to a yield of 15%.

EXAMPLE 13

To 500 ml of fermentation broth of NRRL B-11, 229 containing intracellular lactase was added 50 ml 10% polyethylene imine (T 15, Taihei Sangyo Kaisha) followed by 14 ml 25% glutaraldehyde. Stirring was continued for 30 min. and the preparation was filtered and air-dried. The dried particles were found to contain about 30% of the original lactase activity, and they could be used for repeated batchwise conversions of 4% lactose at 60° C.

EXAMPLE 14

To 300 ml of six times concentrated fermentation broth of *Bacillus pasteurii* ATCC 11 859 (6.3 g dry cells, 9300 urease units/g) was added with stirring 18 ml of 10% polyethylene imine (branched, molecular weight 60 000, PEI 600 from Dow Chemicals), followed by 20 ml 25 glutaraldehyde. After another 60 min. of stirring at room temperature, the immobilized cells were filtered off and air-dried. 13.8 g of dry immobilized cells were obtained with a urease activity of 1900 units/g for a particle size of 300–700$\mu$. This corresponds to an activity yield of about 45%.

EXAMPLE 15

To 100 ml of a 4% (w/v) aqueous suspension of *Bacillus pasteurii* ATCC 11 859 with 230 urease units/ml was added 32 ml 10% polyethylene imine (Polymin HS, BASF) with stirring, followed by 5 ml 25% glutaraldehyde. Stirring was continued for one hour at 4° C., whereafter the cells were filtered off and air-dried. 2.3 g dry preparation contained a urease activity of 3100 units/g (particle size 300–700$\mu$), corresponding to an activity yield of 31 percent.

EXAMPLE 16

0.5 g of the cells immobilized as described in example 14 were packed in a column (1 cm $\phi \times$ 10 cm) and a substrate containing 1% urea (0.01% $MgCl_2$, 10 mM beta-mercaptoethanol) adjusted to pH 9 was passed through the bed at 40° C. 98 percent of the urea could be hydrolysed at a flow rate of 50 ml/h, and the half life of the enzyme activity was about 1000 hrs.

EXAMPLE 17

To 0.25 l fermentation broth of *Leuconostoc oenos* DSM 20252 adjusted to pH 6.5 with NaOH with 14 units malolactic activity liter, was added with stirring 3 ml of 10% polyethylene imine (Polymin P, BASF), followed by 1 ml of 25% glutaraldehyde. Stirring was continued for another 30 min. at 4° C., whereafter the immobilized cells were filtered off, washed with 0.1 M phosphate buffer of pH 6 and water and then freeze-dried. The dried cells had a malo-lactic activity of 3.4 units/g, corresponding to an activity yield of about 40%.

EXAMPLE 18

1.6 g wet cells of *Leuconostoc oenos* DSM 20252 with 96 units malo-lactic activity/g were suspended in 16 ml water and pH was adjusted to 7.0. 1.7 ml 10% polyethylene imine (Polymin P, BASF) was added with stirring, followed by 1.5 ml 25% glutaraldehyde. Stirring was continued for 1 hour at room temperature, whereafter the immobilized cells were filtered, washed with water and air-dried. The dry product (0.5 g) had a malo-lactic activity of 53 units per g, which corresponds to an activity yield of 28 percent.

EXAMPLE 19

4 g dry weight of cells immobilized as described in Example 17 were added to 50 ml 25 mM L-malate in 0.1 M phosphate of pH 5.0 together with 85 $\mu$mol NAD+ and 35 $\mu$mol $MnCl_2$. Total conversion of malate to lactate was obtained in 3 hrs. The procedure could be repeated at least five times without any increase in reaction time.

EXAMPLE 20

0.35 g of the preparation from Example 18 were added to 10 ml 33 mM L-malate in 0.1 M phosphate pH 4.0 together with 17 $\mu$mol NAD+ and 7 $\mu$mol $MnCl_2$. Total conversion of malate to lactate was obtained in six hours, and the procedure could be repeated with fresh malate, NAD+ and $MnCl_2$ at least five times without any increase in reaction times.

What is claimed is:

1. Process for immobilization of an intracellular, glutaraldehyde sensitive enzyme, which process comprises reacting in an aqueous medium microbial cell material containing therein an intracellular glutaraldehyde sensitive enzyme with glutartaldehyde in the presence of a branched polyalkalene imine added to the medium before or simultaneously with the glutaraldehyde, said polyalkalene imine having primary amino groups on the polyalkalene imine molecule at a ratio of primary amine equivalents to aldehyde equivalents in the range of from 0.01:1 to 10:1, and thereafter recovering the resulting immobilized enzyme containing microbial cell preparation.

2. The process of claim 1, wherein the microbial cell material comprises whole microbial cells.

3. The process of claim 1 wherein the microbial cell material is derived from the microorganism of strain NRRL 11240 and contains penicillin V-acylase.

4. The process of claim 1 wherein the microbial cell material is derived from a strain belonging to the species *Bacillus pasteurii* and contains urease.

5. The process of claim 1 wherein the microbial cell material is derived from a strain containing lactase belonging to the species selected from the group consisting of *Kluyveromyces fragilis* and species of strain NRRL B-11, 229.

6. The process of claim 1 wherein the microbial cell material is derived from a strain belonging to the species *Leuconostoc oenos* and contains a malolactic enzyme.

7. The process of claim 1 wherein the aqueous medium is fermentation broth from cultivation of the microorganism source of the microbial cell material.

8. The process of claim 1 wherein the aqueous medium is the aqueous part of a cell sludge separated out of the fermentation broth from cultivation of the microorganism source of the microbial cell material.

9. The process of claim 1 wherein the polyamine is a branched polyethylene imine.

10. The process of claim 9 wherein the branched polyethylene imine has a molecular weight between 500 and 100.000 Daltons.

11. The process of claim 1 wherein the process sequence comprises addition of the polyamine to the microbial material containing aqueous medium and subsequently addition to the glutaraldehyde.

12. The process of claim 1 wherein a ratio glutaraldehyde/microbial cell material (w/w) of from 0.01 to 100.

13. The process of claim 1 wherein the recovered immobilized enzyme containing microbial cell preparation is shaped by extrusion.

14. The process of claim 1 wherein the recovered immobilized enzyme containing microbial cell preparation is shaped to a particle size in the range of from 100 to 1000μ.

15. The immobilized enzyme containing microbial cell preparation produced by the process of claim 1.

* * * * *